United States Patent [19]

Marty et al.

[11] Patent Number: 4,479,023

[45] Date of Patent: Oct. 23, 1984

[54] PROCESS FOR THE OLIGOMERIZATION OF LIGHT OLEFIN FRACTIONS IN THE PRESENCE OF A BORON TRIFLUORIDE CATALYST

[75] Inventors: Claude Marty; Philippe Engelhard, both of Le Havre, France

[73] Assignee: Compagnie Francaise de Raffinage, Paris, France

[21] Appl. No.: 559,328

[22] Filed: Dec. 8, 1983

[51] Int. Cl.$^3$ .................... C07C 3/18; C07C 7/00
[52] U.S. Cl. .................... 585/312; 585/324; 585/329; 585/521; 585/525; 585/810; 585/832; 585/517
[58] Field of Search ............ 585/510, 511, 512, 517, 585/518, 519, 521, 522, 532, 525, 2, 810, 832, 312, 324, 329, 313

[56] References Cited

U.S. PATENT DOCUMENTS

| | | | |
|---|---|---|---|
| 2,139,038 | 12/1938 | Russell | 585/525 |
| 2,148,115 | 2/1939 | Gerhart et al. | 585/525 |
| 2,148,116 | 2/1939 | Gerhart et al. | 585/525 |
| 3,367,987 | 2/1968 | Walsh | 585/521 |
| 3,501,551 | 3/1970 | Heidler et al. | 585/517 |

FOREIGN PATENT DOCUMENTS

| | | | |
|---|---|---|---|
| 1346135 | 1/1963 | France | 585/525 |
| 2493306 | 10/1980 | France | 585/832 |

Primary Examiner—Delbert E. Gantz
Assistant Examiner—A. Pal
Attorney, Agent, or Firm—Curtis, Morris & Safford

[57] ABSTRACT

A process for the oligomerization of olefin fractions where boron trifluoride in the gas phase is contacted with such a fraction, in the absence of a catalyst carrier, under such conditions and for such a length of time that the isobutene and/or butadiene present will polymerize; the boron trifluoride and the isobutene and/or butadiene polymers obtained are then conventionally separated from said fraction; and the olefins of the fraction so purified are oligomerized in the presence of a boron trifluoride catalyst comprising a catalyst carrier.

20 Claims, 1 Drawing Figure

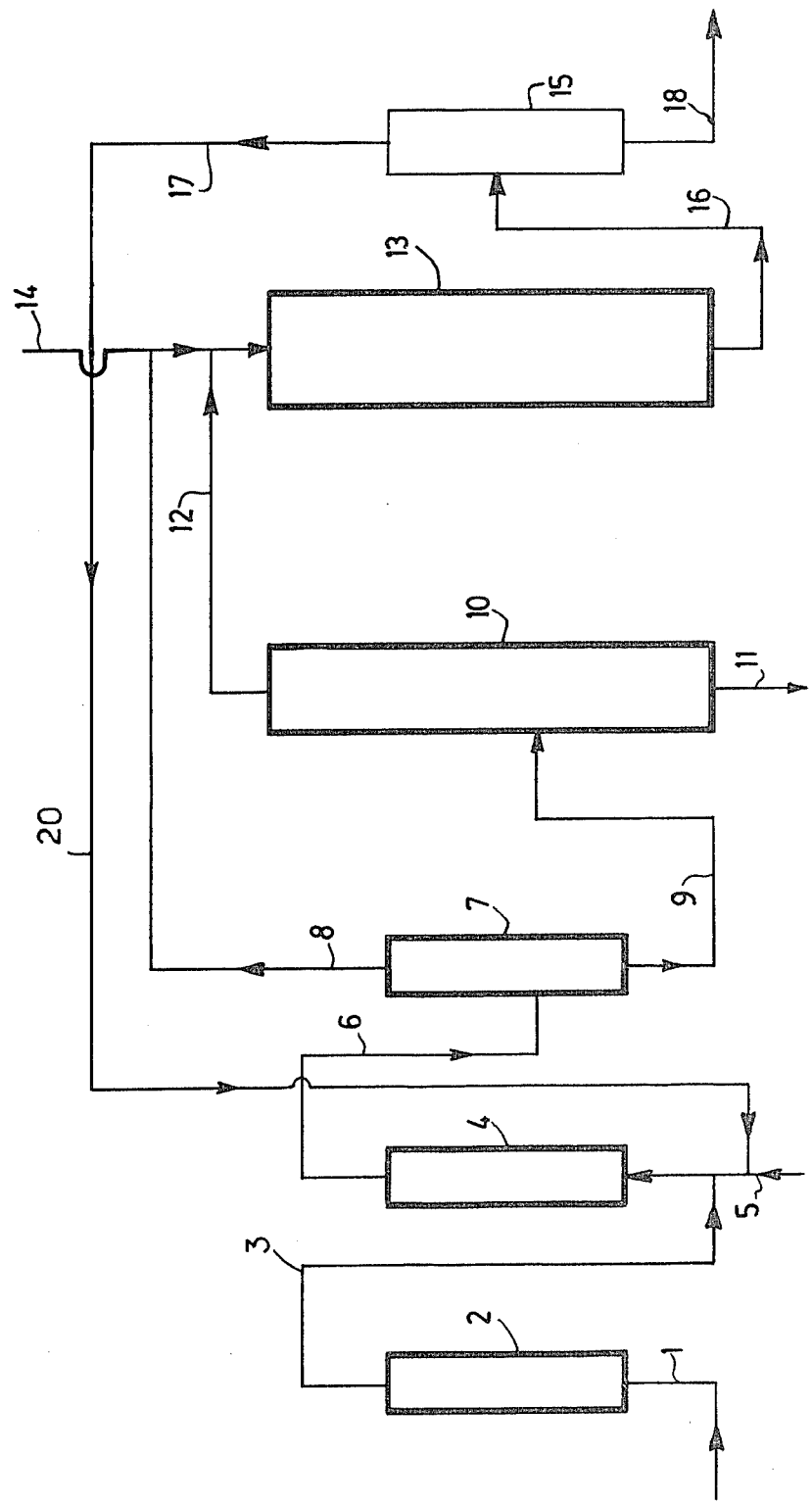

PROCESS FOR THE OLIGOMERIZATION OF LIGHT OLEFIN FRACTIONS IN THE PRESENCE OF A BORON TRIFLUORIDE CATALYST

The present invention relates to a process for the oligomerization of light olefin fractions or mixtures of such fractions.

It is known that as a result of the recent development of cracking reactions for petroleum charge stocks large quantities of olefins having from two to eight carbon atoms, such as ethylene, propylene and the various butenes, pentenes, hexenes, heptenes and octenes, have become available. Of these, the olefin fractions with 3 and 4 carbon atoms, known as the $C_3$, $C_4$ and/or $C_3$-$C_4$ fractions, are in particularly great demand since they can be upgraded by a number of processes. For example, their oligomerization yields, after fractionation, starting materials of interest to the chemical industry, solvents, or lubricating oils; their alkylation results in products having a high octane number which go into the composition of premium-grade gasolines; and their dimerization also yields high-octane products, so far as propylene is concerned, and olefins having from 6 to 8 carbon which are suitable for use as plasticizers, so far as the $C_4$ and/or $C_3$-$C_4$ fractions are concerned.

The ready availability of olefins as starting materials has made it necessary to develop a variety of polymerization catalysts. These include, above all, catalysts based on strong protonic acids such as sulfuric acid, phosphoric acid and hydrofluoric acid, sulfonic resins, Lewis acids, and especially aluminum chloride or fluoride, boron fluoride, zinc fluoride and chloride, stannic chloride and ferric chloride, used in the presence or absence of a promoter such as water, hydrochloric acid, alcohols, glycols or anhydrous ether.

Research on the use of phosphoric catalysts and boron trifluoride catalysts has shown that the latter are more effective. Boron trifluoride catalysts further have the advantage of permitting the reactions to be carried out under milder conditions than other polymerization catalysts, such as phosphoric or hydrofluoric acid catalysts.

For example, French Pat. No. 1,346,135 describes a process for the polymerization of olefinic hydrocarbons in the presence of a catalyst comprising a nearly anhydrous alumina modified with boron trifluoride, which makes it possible to obtain a relatively high polymer yield. However, no mention is made in that patent of a possible choice with respect to the alumina carrier for securing a specificity for a given reaction effluent, and no pretreatment of the charge stock is contemplated.

Now this type of process has several drawbacks:

On the one hand, the olefin fractions used must undergo prior purification since they are susceptible to the presence of many catalyst poisons, such as sulfur, nitrogen, isobutene or butadiene; and while the sulfur derivatives (light mercaptans, $H_2S$ and COS) and the nitrogen derivatives (light amines) can be eliminated at least partially, it is very much more difficult to remove the isobutene and the butadiene, which produce gums and therefore are responsible for the rapid deactivation of the catalysts.

On the other hand, the conversion of the isobutene results in the formation of branched compounds, such as heptenes and octenes, which generally do not meet specifications. While various pretreatments for light olefin charge stocks have been proposed in the literature (for example, in French Pat. No. 2,421,157), these generally are very costly and not very effective since they will not remove the isobutene completely and, above all, will not permit the elimination of traces of butadiene.

Finally, the processes for the oligomerization of olefins which use boron trifluoride on an alumina carrier as catalyst produce an excessive yield of heavy products, which detracts from the economy of the process.

The present invention seeks to overcome these drawbacks by proposing a process for the oligomerization of olefins which, on the one hand, permits the selective extraction in the form of polymers of the isobutene and butadiene present in the fraction, by the action of boron trifluoride and in the absence of a catalyst carrier, and, on the other hand, through the judicious choice of a catalyst carrier, permits the oligomerization of light olefin fractions, and particularly of propylene and butenes or mixtures thereof, to be directed preferentially toward fractions with a low boiling point while limiting the formation of high-boiling polymerization residues.

Applicants have found that in a process for the oligomerization of olefins in the presence of a boron trifluoride polymerization catalyst and in the absence of a catalyst carrier such as alumina it is unexpectedly possible to preferentially polymerize, in a preliminary step in which boron trifluoride is used in the gas phase as catalyst, the butadiene and/or isobutene present without the other olefins of the fraction to be treated being greatly affected, and the polymers so obtained can then readily be separated by means known in the art. The polymers of isobutene and butadiene so separated from the fractions to be treated can then readily be upgraded. Fractionation, optionally followed by hydrogenation, then yields, based on boiling points: Dimers having a high octane number and suitable for use in light gasolines; trimers suitable for use in the formulation of heavy gasolines and of solvents or in petrochemicals; tetramers which after hydrogenation will provide the bases for hydraulic fluids; and, finally, heavier polymers which, also after hydrogenation, are suitable for use as isoparaffinic oils.

Applicants have further found that boron trifluoride catalysts supported on aluminas with low specific surface and low pore volume are conducive to the formation of oligomers having a low boiling point, and that the reaction may be directed preferentially toward yielding polymers having a rather high boiling point by appropriate treatment of the catalyst carrier.

An embodiment of the invention thus is a process for the oligomerization of light olefin fractions or mixtures thereof which is characterized in that boron trifluoride in the gas phase is contacted with the olefin fraction in the absence of a catalyst carrier and under such conditions that the isobutene and butadiene present will polymerize selectively; that the boron trifluoride and the isobutene and butadiene polymers obtained are then conventionally separated from said fraction; and that the olefins of the fraction so purified are then oligomerized in the presence of a boron trifluoride catalyst comprising a catalyst carrier, and more particularly a carrier based on alumina. With a view to obtaining low-boiling oligomers, an alumina-based carrier which has a specific surface ranging from 20 to 120 $m^2/g$ and a pore volume between 0.10 and 0.80 $cm^3/g$ should be selected.

One important advantage of this process is that boron trifluoride is used both in the preliminary step to polymerize the butadiene and the isobutene and in the olefin oligomerization step, so that boron trifluoride can be fed in both for the pretreatment and for the oligomerization, and that the boron trifluoride separated and recovered upon completion of each of these steps can be recycled as desired.

A further advantage of this process is that what distinguishes the two reaction steps from each other is not the temperature, the flow rate or the pressure but the presence or absence of a catalyst carrier for the boron trifluoride. The process of the invention thus reduces the difficult problems of heat regulation posed by this type of reaction to a minimum and eliminates one source of operating errors in the control of industrial units using the process of the invention.

A third advantage of this process is the ability to adapt the oligomer production to the industrial units which follow the production unit. Merely by routing the pretreated charge stock over an appropriate catalyst carrier selected on the basis of its specific surface and its pore volume, the composition of the effluent can be adjusted so that it contains oligomers having a higher or lesser boiling point, as required.

The step of polymerizing the butadiene and the isobutene which constitutes the pretreatment may be carried out under the following conditions:

| | |
|---|---|
| Temperature: | 0 to 100° C. |
| Pressure | 0.1 to 50 bars |
| Boron trifluoride concentration in charge stock to be treated: | 500 to 10,000 ppm |
| Hourly space velocity of charge stock: | 0.1 to 10 volumes per volume of filler material and per hour (v/v/h) |

It will be noted that these operating conditions are not very severe and, in particular, that the temperature may be equal or close to ambient temperature.

Contacting the olefin charge stock with the boron trifluoride may be carried out in an enclosure in the presence of an inert filler material (quartz pieces, glass beads, alumina beads, pebbles, etc.) intended to increase the contact surfaces and to dissipate the heat evolved during the polymerization reaction.

It is thus possible to selectively remove up to about 95 percent of the isobutene and up to 100 percent of the butadiene present in the fractions being treated.

The boron trifluoride can readily be separated after this first step, for example, by flash distillation. It is preferable to separate it first in order to avoid side reactions with the olefins.

The isobutene and butadiene polymers formed can then readily be separated conventionally, for example, in a debutanizer, for purification of the $C_3$ or $C_4$ fractions or mixtures thereof. These polymers are capable of being upgraded for important uses.

The actual oligomerization step is then carried out in the presence of boron trifluoride on a support based on alumina whose specific surface ranges from 20 to 120 $m^2/g$, and preferably from 40 to 100 $m^2/g$, and whose pore volume is between 0.10 and 0.80 $cm^3/g$, and preferably between 0.20 and 0.50 $cm^3/g$.

The oligomerization conditions may be as follows, for example:

| | |
|---|---|
| Temperature: | 0 to 130° C. |
| Pressure: | 0.1 to 50 bars |
| Hourly space velocity of charge stock: | 0.5 to 10 volumes per volume of catalyst and per hour (v/v/h) |

To prepare the catalyst carriers for the oligomerization reaction, the starting aluminas are calcined in the oven for varying lengths of time, as required, until the desired specific-surface and/or pore-volume characteristics are obtained.

It is known (Encyclopedia of Chemical Technology, 3rd ed., vol. 2, pp. 222–228) that the temperature and duration of calcination of an alumina induce structural changes in the alumina which result in modification of its specific surface, and hence of its pore volume. Thus, after an alumina carrier has been treated for an appropriate length of time at temperatures between 400° and 700° C., the resulting specific surface of the carrier will range from 350 to 150 $m^2/g$, which will promote optimum contact with the charge and therefore enhance the effectiveness of the catalyst. Conversely, excessive calcination of the alumina carrier will reduce its effectiveness since the surface area and the pore volume decrease as the temperature is increased.

Contrary to the teachings of the prior art, applicants have found that, without appreciably reducing the total yield of the oligomerization reaction, a decidedly better selectivity for lower-boiling oligomers can be obtained, in the presence of boron trifluoride supported on alumina, when the specific surface and/or the pore volume of the catalyst carrier are limited to the ranges from 20 to 120 $m^2/g$ and from 0.10 to 0.80 $cm^3/g$, respectively, and that appropriate specific-surface and pore-volume values can be obtained by calcination of a starting alumina such as an alumina or a hydrated alumina. Any hydrated alumina, whether prepared by the precipitation of an aluminum salt or obtained directly in a natural or commercial form, may be used, provided that its surface and porosity characteristics equal or exceed those of the desired carrier, and that it contains mainly alumina.

BRIEF DESCRIPTION OF DRAWING

The single FIGURE of the accompanying drawing, which is not limitative, is a flowsheet of the process for the treatment of light olefin fractions in accordance with the invention.

The fresh olefin charge stock ($C_3$, $C_4$ and/or $C_3$–$C_4$ fractions) to be treated is introduced through a line 1 into a tank 2, where it is dried on molecular sieves for the purpose of eliminating any traces of moisture which might react with the boron trifluoride to form borates.

After being mixed with fresh gaseous boron trifluoride introduced through a line 5, the charge stock so dried is conducted through a line 3 to a reactor 4. In view of the heat evolved in the reaction of the isobutene or butadiene with the boron trifluoride, the latter may advantageously be diluted with an inert gas such as nitrogen or argon, or even with butane or propane.

With a view to increasing the contact surfaces and to retaining the heat generated by the reaction, the reactor 4 may contain an inert contact material, such as quartz pieces, glass beads, sand, alumina beads, etc. Under the operating conditions set forth above, this contact material can be maintained at a temperature of about 20° C., for example.

The effluent from the reactor 4 is conducted through a line 6 to a flash drum 7, in which the gaseous boron trifluoride is separated overhead through a line 8 from the fraction being treated and piped to a reactor 13. At the bottom of the flash drum 7, the olefin fraction being treated, which contains polymers of butadiene and isobutene, is recovered through a line 9 and conducted to a separating column 10.

From the bottom of said column, through a line 11, the polymerized isobutene and butadiene are withdrawn, and from the top of the column, through a line 12, the $C_4$ or $C_3$–$C_4$ fraction so purified, i.e., freed of the isobutene and butadiene with which it was contaminated. The fraction so treated may then be conducted through line 12 to the oligomerization reactor 13, which contains an alumina carrier previously saturated with a boron trifluoride stream, optionally diluted with an inert gas such as argon or nitrogen.

To maintain the activity of the catalyst in reactor 13, a light boron trifluoride stream is injected into said reactor through a line 14 at the same time as the olefin charge stock. Said boron trifluoride stream is formed of the boron trifluoride which was separated in drum 7 and conducted through line 8. Fresh makeup boron trifluoride may also be introduced through line 14.

The effluent from reactor 13 is conducted through a line 16 to a separator 15. In the latter, the boron trifluoride present in the effluent is separated from the oligomers and recycled to line 5 through a line 17. The oligomers recovered at the bottom of separator 15 through a line 18 are then fractionated in the usual manner into various fractions on the basis of their boiling temperatures.

Prior to such fractionation, the oligomers coming from separator 15 may be decontaminated, if necessary, with a view to removing any traces of boron trifluoride. The decontamination treatment may be carried out conventionally, for example, by passage over alumina or bauxite, or by washing with soda.

The examples which follow, which are in no wise limitative, will serve to illustrate the practice of the invention.

EXAMPLE 1

An olefinic charge stock coming from a catalytic cracking unit and having the composition given in Table 1 below was treated in accordance with the invention.

TABLE 1

| Constituents | Volume percent | Weight percent |
| --- | --- | --- |
| Saturated hydrocarbons | 53.4 | 55.6 |
| Olefins including: | 46.6 | 44.4 |
| Butene-1 | 6.1 | 6.3 |
| Isobutene | 8.5 | 8.9 |
| trans-Butene-2 | 9.7 | 10.1 |
| cis-Butene-2 | 5.8 | 6.0 |
| Propylene | 16.5 | 13.1 |
| 1,3-Butadiene | 500 ppm | 600 ppm |

The treating conditions in reactor 4 were as follows:

| | |
| --- | --- |
| Temperature: | 20° C. |
| Pressure: | 30 bars |
| Hourly space velocity of charge stock: | 3 v/v/h |
| Boron trifluoride concentration (based on charge stock): | 2,000 ppm |
| Nature of contact material: | 50 cm³ of glass beads |

-continued

| | |
| --- | --- |
| | 2 mm in diameter |

The gaseous effluent leaving separating column 10 through line 12 had the composition given in Table 2 which follows.

TABLE 2

| Constituents | Volume percent | Weight percent |
| --- | --- | --- |
| Saturated hydrocarbons | 61 | 62 |
| Olefins including: | 39 | 37.4 |
| Butene-1 | 6.7 | 6.9 |
| Isobutene | 0.8 | 0.9 |
| trans-Butene-2 | 9.3 | 9.7 |
| cis-Butene-2 | 5.7 | 5.9 |
| Propylene | 16.5 | 14.0 |
| Butadiene | 200 ppm | 200 ppm |

Pretreatment permitted the specific removal rate set forth in Table 3 below to be obtained for each olefin.

TABLE 3

| Olefin | Specific removal rate (Weight percent) |
| --- | --- |
| Butene-1 | 3 |
| Isobutene | 92 |
| Butene-2 | 16 |
| Propylene | 5 |
| Butadiene | 70 |

This treatment thus had the effect of removing 92 percent of the isobutene and 70 percent of the butadiene in the charge stock.

The purified charge stock, whose composition is given in Table 2, was then treated in oligomerization reactor 13. The reactor contained a boron trifluoride catalyst supported on alumina of low specific surface and low pore volume. This catalyst had been prepared in the following manner:

The starting material was a commercial alumina which had a predominantly $\eta$ structure and whose characteristics were as follows:

| | |
| --- | --- |
| Specific surface: | 400 m²/g |
| Pore volume: | 0.46 cm³/g |
| Pore radius: | 20 Å |
| Particle size (after screening) | 2 to 2.5 mm |
| Apparent density: | 0.80 g/cm³ |

This alumina was calcined in the oven for 24 hours at a temperature of 1000° C. After calcination, it had a $\theta$ plus $\alpha$ structure. Its specific surface was 43 m²/g, and its pore volume, 0.20 cm³/g.

The catalyst carrier so prepared was then placed in the reactor 13 and saturated by the passage of a stream of gaseous boron trifluoride diluted to 10 percent with nitrogen under the following conditions:

| | |
| --- | --- |
| Length of Time: | 24 hours |
| Temperature: | 130° C. |
| Pressure: | 25 bars |
| Flow rate: | 2.5 standard liters/hour for 50 cm³ of carrier diluted with 50 cm³ of glass beads of the same particle size. |

On completion of this operation, the pretreated charge was oligomerized in reactor 13 under the following conditions:

| | |
|---|---|
| Constant pressure: | 30 bars |
| Constant BF₃ concentration: | 2,000 ppm (based on charge stock) |
| Temperature: | 75° C. |
| Hourly space velocity of charge stock: | 6 v/v/h |

The effluent leaving the reactor 13 was collected in the separator 15, where a gaseous phase containing the unreacted products and the boron trifluoride was obtained, which was conducted through line 17 and recycled through line 5, as well as a liquid phase containing the products of oligomerization. The latter were then fractionated into four fractions, namely, a 60°-120° C. fraction,
a 120°-220° C. fraction,
a 220°-250° C. fraction, and
a 250°-320° C. fraction,
leaving a residue with a boiling point above 320° C.

The case of a charge stock not subjected to a pretreatment with gaseous boron trifluoride has also been studied, and Table 4 which follows gives the oligomer yields and selectivities obtained with and without pretreatment.

TABLE 4

| | Without pretreatment | With pretreatment |
|---|---|---|
| Oligomer yield (g/100 g of olefins) | 80 | 83 |
| Oligomer selectivity (Weight percent) | | |
| 60–120° C. fraction | 20 | 40 |
| 120–220° C. fraction | 46.6 | 40.8 |
| 220–250° C. fraction | 12.7 | 6.9 |
| 250–320° C. fraction | 13.2 | 9.3 |
| Residue over 320° C. | 7.5 | 3 |

In the case of this oligomerization, the specific removal rates set forth for each olefin in Table 5 which follows were obtained.

TABLE 5

| | Rate of removal of each olefin (Weight percent) | |
|---|---|---|
| Olefins | Without pretreatment | With pretreatment |
| Butene-1 | 93 | 92 |
| Isobutene | 100 | 100 |
| Butenes-2 | 71 | 68 |
| Propylene | 94 | 95 |
| Butadiene | 100 | 100 |

EXAMPLE 2

A charge stock having the composition given in Table 6 which follows was treated in accordance with the invention.

TABLE 6

| Constituents | Volume percent | Weight percent |
|---|---|---|
| Saturated hydrocarbons | 54.1 | 56.3 |
| Olefins including: | 45.9 | 43.7 |
| Propylene | 16.4 | 13.0 |
| Butene-1 | 1 | 6.2 |

TABLE 6-continued

| Constituents | Volume percent | Weight percent |
|---|---|---|
| Isobutene | 8.0 | 8.4 |
| trans-Butene-2 | 9.6 | 10.1 |
| cis-Butene-2 | 6.8 | 6.0 |
| Butadiene | 500 ppm | 600 ppm |

This charge was treated in reactor 4 under the conditions set forth in Example 1, namely:

| | |
|---|---|
| Temperature: | 20° C. |
| Pressure: | 30 bars |
| Hourly space velocity of charge stock: | 3 v/v/h |
| Baron trifluoride concentration (based on charge stock): | 2,000 ppm |
| Nature of contact material: | 50 cm³ of glass beads 2 mm in diameter |

The composition of the pretreated charge is given in Table 7 below.

TABLE 7

| | Composition | |
|---|---|---|
| Constituents | Volume percent | Weight percent |
| Saturated hydrocarbons | 62.1 | 63.8 |
| Olefins including: | 37.9 | 36.2 |
| Propylene | 16.5 | 14.0 |
| Butene-1 | 6.6 | 6.7 |
| Isobutene | 0.4 | 0.4 |
| trans-Butene-2 | 8.9 | 9.4 |
| cis-Butene-2 | 5.5 | 5.7 |
| Butadiene | 0 | 0 |

It will be noted that all of the butadiene in the original charge stock was removed. 92 percent of the isobutene was also removed from the charge stock.

The purified charge, whose composition is given in Table 7, was then treated in reactor 13 under the conditions specified in Example 1, except that the catalyst was supported on alumina of structure η, a specific surface of 201 m²/g, and a pore volume of 0.41 cm³/g. This alumina had been prepared by calcination for 4 hours at 600° C. of the commercial alumina whose characteristics are given in Example 1.

After treatment in the reactor 13 and separation of the effluents in the separator 15, a liquid phase was collected and fractionated into various fractions as in Example 1.

An identical charge which had not been pretreated in reactor 4 was also treated in reactor 13.

An identical pretreatment and treatment were then carried out in which the alumina was replaced with an alumina calcined under the conditions of Example 1.

The oligomer yields and the selectivites obtained in these three cases are given in Table 8 which follows.

TABLE 8

| | High-surface alumina (η alumina) | | Low-surface alumina (θ and α alumina) |
|---|---|---|---|
| | Without pretreatment | With pretreatment | With pretreatment |
| Oligomer yield (g/100 g of olefins) | 92 | 93 | 85 |
| Oligomer selectivity | | | |

TABLE 8-continued

|  | High-surface alumina (η alumina) | | Low-surface alumina (θ and α alumina) |
| --- | --- | --- | --- |
|  | Without pretreatment | With pretreatment | With pretreatment |
| (Weight percent) | | | |
| 60–120° C. fraction | 14.9 | 20 | 38 |
| 120–220° C. fraction | 36.7 | 40 | 41.2 |
| 220–250° C. fraction | 15.4 | 14.4 | 7.8 |
| 250–320° C. fraction | 19.8 | 17.6 | 9.2 |
| Residue over 320° C. | 13.2 | 8.0 | 3.8 |

The conversion rate for each olefin in the three above oligomerization cases is given in Table 9 which follows.

TABLE 9

| | Conversion rate for each olefin (weight percent) | | |
| --- | --- | --- | --- |
| | High-surface alumina | | |
| Olefins | Without pretreatment | With pretreatment | Low-surface alumina With pretreatment |
| Butene-1 | 100 | 98 | 93 |
| Isobutene | 100 | 100 | 100 |
| Butenes-2 | 74 | 88 | 68 |
| Propylene | 100 | 100 | 95 |
| Butadiene | 100 | 100 | 100 |

As is apparent from these results, the selectivity for the 60°–120° C. light fraction is appreciably increased and the selectivity for a residue (of over 320° C.) markedly reduced when, in accordance with the invention, a catalyst of low specific surface is used after the charge stock has been pretreated with gaseous boron trifluoride for the purpose of selectively polymerizing the butadiene and isobutene contained therein.

We claim:

1. A process for the oligomerization of a light olefin fraction containing isobutene or butadiene which favors the yield of lower boiling point oligomers, which comprises:
   as a pretreatment, contacting the olefin fraction with boron trifluoride in a gas phase in the absence of a catalyst carrier such that isobutene and/or butadiene are selectively polymerized;
   separating boron trifluoride and the resulting isobutene and/or butadiene polymers from the other substantially unreacted olefins of said light olefin fraction to form a purified olefin fraction from which most of the isobutene and butadiene has been removed;
   treating the purified fraction with a boron trifluoride catalyst containing an alumina catalyst carrier having a specific surface of from 20 to 120 m²g and a pore volume between 0.10 and 0.80 cm³/g such that the light olefins are oligomerized producing an oligomeric product significantly richer in the 60°–120° C. light fraction and with significantly less of a residue having a boiling point over 320° C. than a product produced by the same oligomerization process which omits said pretreatment.

2. A process according to claim 1, wherein about 92% or more of the isobutene and about 70% or more of the butadiene is removed to give said purified olefin fraction, and said oligomerized product is about 38% or more by weight of said 60°–120° C. light fraction and about 3.8% or less by weight of said 320° C. residue.

3. A process according to claim 2, wherein the olefin fraction is contacted with the gaseous boron trifluoride in the presence of an inert filler material.

4. A process according to claim 1, wherein the olefin fraction is contacted with the gaseous boron trifluoride at a temperature ranging from 0° to 100° C. and a pressure between 0.1 to 50 bars.

5. A process according to claim 2, wherein the olefin fraction is contacted with the gaseous boron trifluoride at a temperature ranging from 0° to 100° C. and a pressure between 0.1 to 50 bars.

6. A process according to claim 1, wherein in the separating step the boron trifluoride is separated from said fraction before the isobutene and/or butadiene polymers are separated.

7. A process according to claim 2, wherein in the separating step the boron trifluoride is separated from said fraction before the isobutene and/or butadiene polymers are separated.

8. A process according to claim 4, wherein in the separating step the boron trifluoride is separated from said fraction before the isobutene and/or butadiene polymers are separated.

9. A process according to claim 5, wherein in the separating step the boron trifluoride is separated from said fraction before the isobutene and/or butadiene polymers are separated.

10. A process according to claim 6, wherein the boron trifluoride is separated from said fraction by a process including flash distillation.

11. A process according to claim 9, wherein the boron trifluoride is separated from said fraction by a process including flash distillation.

12. A process according to claim 1, wherein the catalyst carrier has a specific surface of from 40 to 100 m²/g and a pore volume between 0.20 and 0.50 cm³/g such that the selectivity of the oligomerization is directed toward the production of dimerized or trimerized effluents.

13. A process according to claim 2, wherein the catalyst carrier has a specific surface of from 40 to 100 m²/g and a pore volume between 0.20 and 0.50 cm³/g such that the selectivity of the oligomerization is directed toward the production of dimerized or trimerized effluents.

14. A process according to claim 2, further comprising calcining the catalyst carrier before the treating step to adjust its specific surface and pore volume.

15. A process according to claim 12, further comprising calcining the catalyst carrier before the treating step to adjust its specific surface and pore volume.

16. A process according to claim 13, further comprising calcining the catalyst carrier before the treating step to adjust its specific surface and pore volume.

17. A process according to claim 2, wherein the treating step is carried out at a pressure ranging from 0.1 to 50 bars and at a temperature ranging from 0° to 130° C.

18. A process according to claim 2, further comprising recovering boron trifluoride after the treating step and recycling the boron trifluoride from the separating step and/or the recovering step into the contacting step and/or the treating step.

19. A process according to claim 2, wherein the contacting step and the treating step are carried out under substantially identical operating conditions.

20. A process according to claim 2, wherein said light olefin fraction is substantially only $C_3$ and/or $C_4$ olefins.

* * * * *